United States Patent [19]

Schwenner et al.

[11] Patent Number: 5,409,932
[45] Date of Patent: Apr. 25, 1995

[54] PIPERAZINE-SUBSTITUTED PYRROLOANTHRACENES

[75] Inventors: Eckhard Schwenner, Wuppertal, Germany; Gaetan Ladouceur, Hamden, Conn.; Hans-Joachim Kabbe, Leverkusen, Germany; Thomas M. Aune, Hamden, Conn.

[73] Assignee: Bayer AG, Leverkusen, Germany

[21] Appl. No.: 164,499

[22] Filed: Dec. 9, 1993

[51] Int. Cl.⁶ .................. A61K 31/495; C07D 403/00
[52] U.S. Cl. ..................... 514/253; 544/373; 514/825
[58] Field of Search .......... 544/373; 514/253

[56] References Cited

U.S. PATENT DOCUMENTS 4,732,984  3/1988  Abou-Gharbia et al. ........... 544/295
4,804,751  2/1989  Abou-Gharbia et al. ........... 544/295

FOREIGN PATENT DOCUMENTS 9204015  3/1992  WIPO.

OTHER PUBLICATIONS

Stites et al, Basic and Clinical Immunology 7th Edition, pp. 722 and 784 (1991).
Blue, Daley, Levine, Craig and Schlossmann, "Biosynthesis and Surface Expression of T8 by Peripheral Blood T4+ in Vitro" (1986).
Connolly, Stecher, Speight, Becker and Rathman, "Differential effects of anti-arthritic agents on subnormal plasma iron levels . . . rats" (1989).
Sokoloff, "Animal Models of Rheumatoid Arthritis" International Review of Experimental Pathology, vol. 26 (1984).
Aune, Kelley, Ranges and Bombara, "Serotonin-Activated Signal-Transduction Via Serontonin Receptors and Jurkat Cells" (1990).
Billingham, Butler and Colston, "A Mycobacterial 65-kD Heat Shock Protein Induces Antigen-Specific Suppression . . . " Brief Definitive Report (1990).

Primary Examiner—Cecilia Tsang
Attorney, Agent, or Firm—Sprung Horn Kramer & Woods

[57] ABSTRACT

The piperazine-substituted pyrroloanthracenes are prepared by reacting either furanoanthracenes with piperazinalkylamines or reacting unsubstituted pyrroloanthracenes first with dihalogenoalkyl compounds and then with appropriately substituted piperazines or by reacting furan derivatives first with piperazinalkylamines and then condensing with anthracenes. The new compounds can be employed as active ingredients in medicaments, in particular in immunomodulators.

11 Claims, No Drawings

PIPERAZINE-SUBSTITUTED PYRROLOANTHRACENES

The present invention relates to piperazine-substituted pyrroloanthracenes, processes for their preparation and their use in medicaments.

The publication U.S. Pat. No. 4,804,751 A discloses polycyclic dicarboximides having an antipsychotic and anxiolytic action.

In most theories about autoimmune diseases, T lymphocytes are mentioned as initiators of many cellular processes which lead to tissue destruction and to symptoms which are associated with specific autoimmune diseases [Paul, E. W. 1984, Fundamental Immunology, Ravens Press, New York]. Rheumatoid arthritis is an example of such a disease and adjuvant-induced arthritis in the rat is regarded as a representative animal model thereof [Lombardino, J. G. 1985, Nonsteroidal Antiinflammatory Drugs, John Wiley & Sons, New York]. For the rat adjuvant arthritis model, it has been shown with the aid of a large number of studies that T cells are involved in the progression of the disease. Additionally, T cells from rats with adjuvant disease transfer this disease to healthy animals in the absence of any source of antigen or other inflammatory factors.

As a consequence, the inhibition of the T cell function or T cell activation should positively affect both adjuvant arthritis in the rat and also the course of the disease in various human autoimmune diseases.

Recently, a serotonin-type receptor was identified on Jurkart cells [Aune, T., M. Kelley, U. A. Ranges, G. E. Bombera, M. P. 1990, J. Immunol. 145, 1826], from which it is assumed that it regulates T cell function. It is therefore assumed that selective antagonists of this receptor inhibit T cell proliferation.

The present invention relates to piperazine-substituted pyrroloanthracenes of the general formula (I)

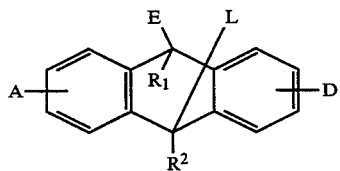

in which
- A and D are identical or different and represent hydrogen, hydroxyl, halogen, cyano, carboxyl, nitro, trifluoromethyl or trifluoromethyloxy, or represent straight-chain or branched alkyl or alkoxy in each case having up to 8 carbon atoms,
- $R^1$ and $R^2$ are identical or different and represent hydrogen, halogen, cyano, formyl, phenyl or hydroxyl, or represent straight-chain or branched alkoxy having up to 8 carbon atoms, or represent straight-chain or branched alkyl or alkenyl in each case having up to 8 carbon atoms, each of which is optionally substituted up to 2 times by identical or different hydroxyl, nitro, phenyl or halogen, by straight-chain or branched alkoxy having up to 6 carbon atoms or by a group of the formula —$NR^3R^4$,
  in which
  $R^3$ and $R^4$ are identical or different and denote hydrogen, straight-chain or branched alkyl having up to 6 carbon atoms or phenyl,
- E and L together form a heterocyclic radical of the formula

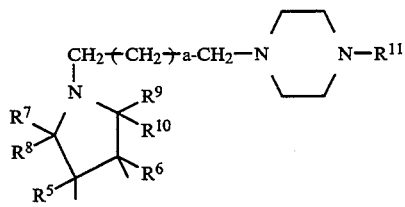

in which
- $R^5$ and $R^6$ are identical or different and denote hydrogen, halogen, phenyl or straight-chain or branched alkyl having up to 8 carbon atoms, which is optionally substituted by carboxyl or by straight-chain or branched alkoxycarbonyl having up to 6 carbon atoms,
- $R^7$, $R^8$, $R^9$ and $R^{10}$ are identical or different and denote hydrogen or straight-chain or branched alkyl having up to 6 carbon atoms, or
- $R^7$ and $R^8$ and/or $R^9$ and $R^{10}$ in each case together form the radical of the formula=O,
- a denotes a number 0, 1, 2, 3, 4, 5 or 6,
- $R^{11}$ denotes aryl having 6 to 10 carbon atoms, which is optionally substituted up to 3 times by identical or different halogen, hydroxyl, nitro, cyano, trifluoromethyl, trifluoromethoxy or by straight-chain or branched alkyl or alkoxy in each case having up to 8 carbon atoms, and their salts.

Physiologically acceptable salts are preferred in the context of the present invention. Physiologically acceptable salts of the piperazine-substituted pyrroloanthracenes can be salts of the substances according to the invention with mineral acids, carboxylic acids or sulfonic acids. Particularly preferred salts, for example, are those with hydrochloric acid, hydrobromic acid, sulfuric acid, phosphoric acid, methanesulfonic acid, ethanesulfonic acid, toluenesulfonic acid, benzenesulfonic acid, naphthalinedisulfonic acid, acetic acid, propionic acid, lactic acid, tartaric acid, citric acid, fumaric acid, maleic acid or benzoic acid.

Salts in the context of the present invention are additionally salts of the monovalent metals such as alkali metals and the ammonium salts. Sodium, potassium and ammonium salts are preferred.

The compounds according to the invention exist in stereoisomeric forms, which either behave as image and mirror image (enantiomers), or which do not behave as image and mirror image (diastereomers). The invention relates both to the antipodes and to the racemic forms as well as to the diastereomer mixtures. Like the diastereomers, the racemic forms can be separated into the stereoisomerically uniform constituents in a known manner.

Preferred compounds of the general formula (I) are those
in which
A and D are identical or different and represent hydrogen, hydroxyl, fluorine, chlorine, bromine, carboxyl, nitro, trifluoromethyl, trifluoromethoxy or represent straight-chain or branched alkyl or alkoxy in each case having up to 6 carbon atoms, $R^1$ and $R^2$ are identical or different and represent hydrogen, fluorine, chlorine, bromine, cyano, formyl, phenyl or hydroxyl, or represent straight-chain or branched alkoxy having up to 6 carbon atoms, or represent straight-chain or branched alkyl or alkenyl in each case having up to 6 carbon atoms, each of which is optionally substituted up to 2 times by identical or different hydroxyl, nitro, phenyl, fluorine, chlorine or bromine, by straight-chain or branched alkoxy having up to 4 carbon atoms or by a group of the formula —$NR^3R^4$, in which $R^3$ and $R^4$ are identical or different and denote hydrogen, straight-chain or branched alkyl having up to 4 carbon atoms or phenyl, E and L together form a heterocyclic radical of the formula

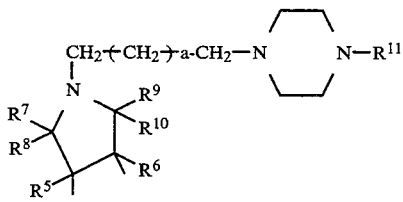

in which $R^5$ and $R^6$ are identical or different and denote hydrogen, fluorine, chlorine, bromine, phenyl or straight-chain or branched alkyl having up to 6 carbon atoms, which is optionally substituted by carboxyl or by straight-chain or branched alkoxycarbonyl having up to 4 carbon atoms, $R^7$, $R^8$, $R^9$ and $R^{10}$ are identical or different and denote hydrogen or straight-chain or branched alkyl having up to 4 carbon atoms, or $R^7$ and $R^8$ and/or $R^9$ and $R^{10}$ in each case together form the radical of the formula =O, denotes a number 0, 1, 2, 3, 4 or 5, $R^{11}$ denotes phenyl which is optionally substituted up to 3 times by identical or different fluorine, chlorine, bromine, hydroxyl, nitro, cyano, trifluoromethyl or trifluoromethoxy or by straight-chain or branched alkyl or alkoxy in each case having up to 6 carbon atoms, and their salts.

Particularly preferred compounds of the general formula (I) are those in which

A and D are identical or different and represent hydrogen, hydroxyl, fluorine, chlorine, bromine or straight-chain or branched alkyl having up to 4 carbon atoms, $R^1$ and $R^2$ are identical or different and represent hydrogen, fluorine, chlorine, bromine, cyano, formyl, phenyl or hydroxyl, or represent straight-chain or branched alkoxy having up to 4 carbon atoms, or represent straight-chain or branched alkyl or alkenyl in each case having up to 4 carbon atoms, each of which is optionally substituted up to 2 times by identical or different hydroxyl, nitro, phenyl, fluorine, chlorine or bromine, by straight-chain or branched alkoxy having up to 3 carbon atoms or by amino or aminomethyl, E and L together form a heterocyclic radical of the formula

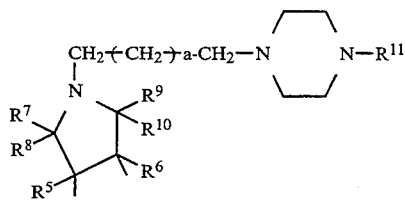

in which $R^5$ and $R^6$ are identical or different and denote hydrogen, fluorine, chlorine, bromine, phenyl or straight-chain or branched alkyl having up to 4 carbon atoms, which is optionally substituted by carboxyl or by straight-chain or branched alkoxycarbonyl having up to 3 carbon atoms, $R^7$, $R^8$, $R^9$ and $R^{10}$ are identical or different and denote hydrogen or straight-chain or branched alkyl having up to 3 carbon atoms, or $R^7$ and $R^8$ and/or $R^9$ and $R^{10}$ in each case together form the radical of the formula =O, a denotes a number 0, 1, 2, 3 or 4, $R^{11}$ denotes phenyl which is optionally substituted up to 3 times by identical or different fluorine, chlorine, bromine, hydroxyl, nitro, cyano, trifluoromethyl or trifluoromethoxy or by straight-chain or branched alkyl or alkoxy in each case having up to 4 carbon atoms, and their salts.

Processes for the preparation of the compounds of the general formula (I) according to the invention have additionally been found, which comprise

[A] reacting compounds of the general formula (II)

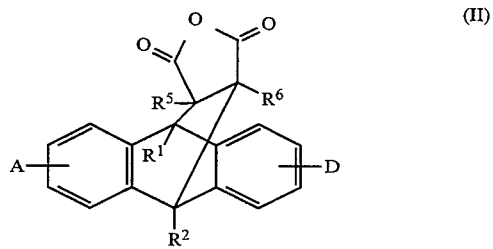

in which

A, D, $R^1$, $R^2$, $R^5$ and $R^6$ have the abovementioned meaning, with compounds of the general formula (III)

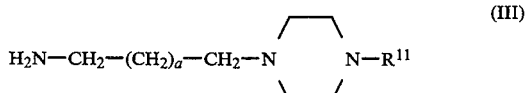

in which a and $R^{11}$ have the abovementioned meaning, in inert solvents, in the presence of a base and/or auxiliary, if appropriate under a protective gas atmosphere, or

[B] converting compounds of the general formula (IV)

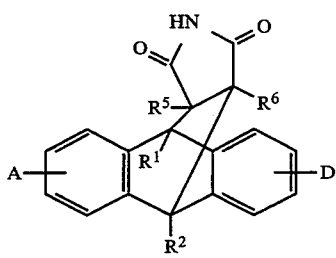

(IV)

in which
A, D, $R^1$, $R^2$, $R^5$ and $R^6$ have the abovementioned meaning,
first by reaction with compounds of the general formula (V)

$$Q-CH_2-(CH_2)_a-CH_2-S \qquad (v)$$

in which
a has the abovementioned meaning,
Q represents halogen or a typical leaving group, but preferably bromine, and
S has the abovementioned meaning of Q or represents carboxyl or an activated carboxylic radical,
in inert solvents, if appropriate in the presence of a base, into the compounds of the general formula (VI)

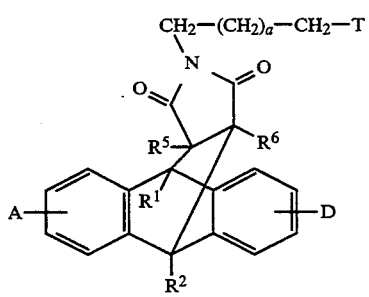

(VI)

in which
A, D, a, $R^1$, $R^2$, $R^5$ and $R^6$ have the abovementioned meaning, and
T includes the abovementioned scope of meaning of Q and S,
and in a second step, likewise in the presence of a base and of a solvent, reacting with compounds of the general formula (VII)

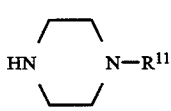

(VII)

in which
$R^{11}$ has the abovementioned meaning, or
[C] first converting compounds of the general formula (III) by reaction with compounds of the general formula (VIII)

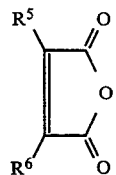

(VIII)

in which
$R^5$ and $R^6$ have the abovementioned meaning, into the compounds of the general formula (IX)

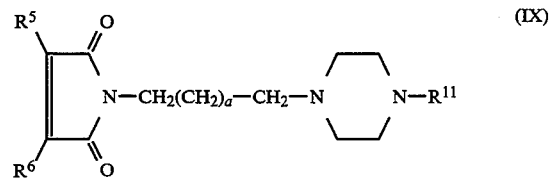

(IX)

in which
$R^5$, $R^6$, $R^{11}$ and a have the abovementioned meaning,
and then reacting with anthracenes of the general formula (X)

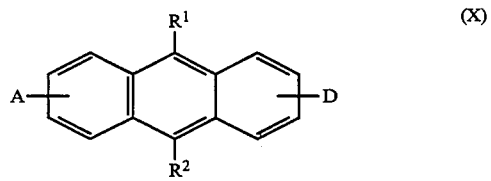

(X)

in which
A, D, $R^1$ and $R^2$ have the abovementioned meaning, in inert solvents,
and in the case where $R^7$ and $R^8$ and/or $R^9$ and $R^{10}$ do not in each case together form the radical of the formula=O,
reducing by customary methods,
and optionally varying the abovementioned substituents according to known methods.

The processes according to the invention can be illustrated by way of example by the following reaction schemes:

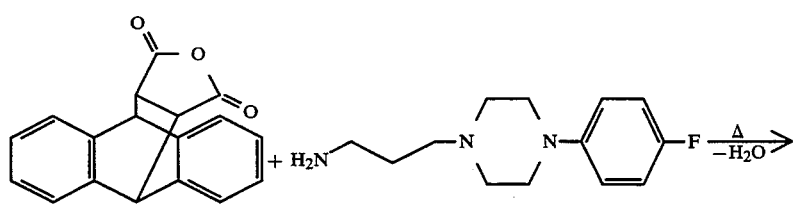

[A]

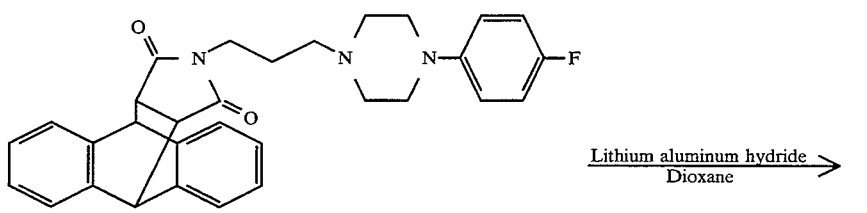
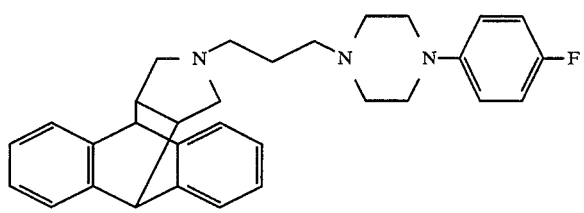
[B]
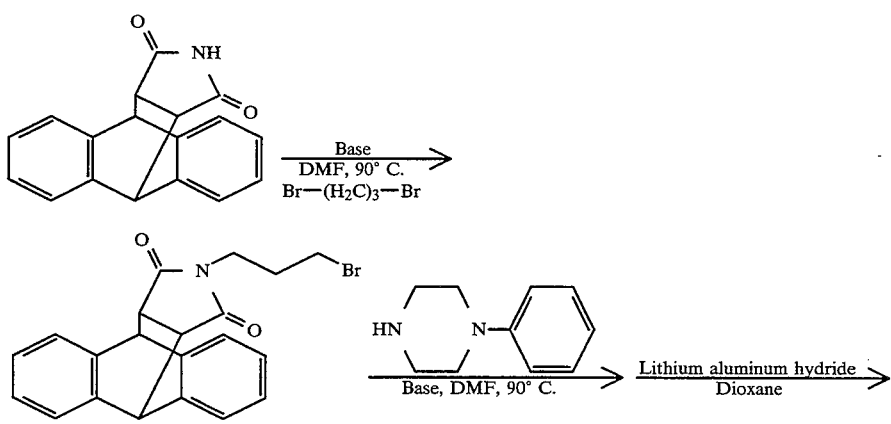
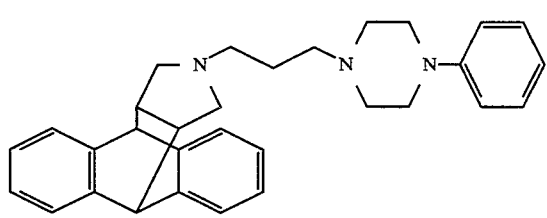
[C]
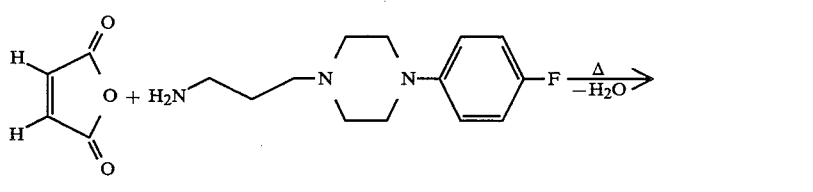
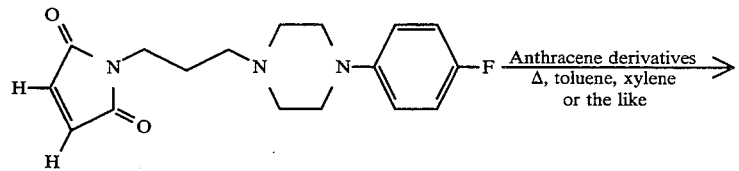
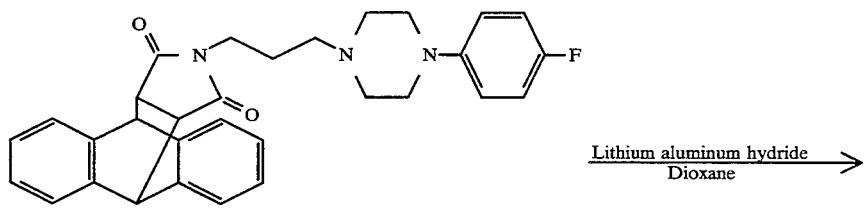

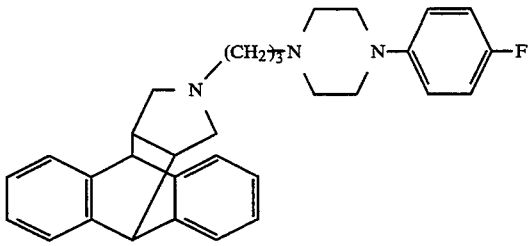

Suitable solvents for the processes are customary organic solvents which do not change under the reaction conditions. These preferably include ethers such as diethyl ether, dioxane, tetrahydrofuran, glycol dimethyl ether, 1,2-dimethoxyethane or hydrocarbons such as benzene, toluene, xylene, hexane, cyclohexane or mineral oil fractions, or halogenohydrocarbons such as dichloromethane, trichloromethane, tetrachloromethane, dichloroethylene, trichloroethylene or chlorobenzene, or ethyl acetates, triethylamine, pyridine, dimethyl sulfoxide, dimethyl formamide, hexamethylphosphoramide, acetonitrile, acetone or nitromethane. It is also possible to use mixtures of the solvents mentioned. Xylene is preferred.

Bases which can be employed for the processes according to the invention are in general inorganic or organic bases. These preferably include alkali metal hydroxides or alkaline earth metal hydroxides such as, for example, sodium hydroxide, potassium hydroxide or lithium hydroxide, barium hydroxide, alkali metal or alkaline earth metal carbonates such as sodium carbonate, potassium carbonate, calcium carbonate or cesium carbonate, or alkali metal or alkaline earth metal alkoxides such as sodium methoxide or potassium methoxide or potassium tert-butoxide, or lithium diisopropylamide (LDA), or organic amines (trialkyl($C_1$-$C_6$)amines) such as triethylamine, or heterocycles such as 1,4-diazobicyclo[2.2.2]octane (DABCO), 1,8-diazabicyclo[5.4.0]undec-7-ene (DBU), pyridine, diaminopyridine, methylpiperidine or morpholine. It is also possible to employ alkali metals, such as sodium, or their hydrides such as sodium hydride as bases. Potassium carbonate, sodium hydride, potassium tert-butoxide and cesium carbonate are preferred.

In general, the base is employed in an amount from 0.05 mol to 10 mol, preferably from 1 mol to 2 mol, in each case relative to 1 mol of the compounds of the general formulae (III), (V) and (VII).

Suitable auxiliaries for the activation of the carboxylic acid function in the compounds of the general formula (V) and for the Diels-Alder reaction are Lewis acids such as, for example, zinc chloride, titanium tetrachloride, boron tribromide, aluminum chloride or lithium perchlorate or thionyl chloride, phosphorus trichloride, phosphorus pentachloride, phosphorus tribromide or oxalyl chloride. Carbonyl compounds such as carbonyldiimidazole or 1,2-oxazolium compounds such as 2-ethyl-5-phenyl-1,2-oxazolium-3-sulfonate or propanephosphonic anhydride or isobutyl chloroformate or benzotriazolyloxy-tris-(dimethylamino)phosphonium hexafluorophosphate or diphenyl phosphoramidate or methanesulfonyl chloride are additionally suitable, if appropriate in the presence of bases such as triethylamine or N-ethylmorpholine or N-methylpiperidine or dicyclohexylcarbodiimide and N-hydroxysuccinimide.

The processes according to the invention are in general carried out in a temperature range from 0° C. to +180° C., preferably from +20° C. to +150° C.

The process according to the invention is in general carried out at normal pressure. However, it is also possible to carry out the process at elevated pressure or at reduced pressure (e.g. in a range from 0.5 to 5 bar).

Carbonyl functions are in general reduced using complex hydrides, such as lithium aluminum hydride or sodium borohydride, preferably using lithium aluminum hydride in inert solvents such as ethers or hydrocarbons or their mixtures, preferably in ethers such as, for example, diethyl ether, tetrahydrofuran or dioxane, in a temperature range from 0° C. to +150° C., preferably from +20° C. to +100° C., at normal pressure.

The abovementioned derivatizations of the substituents $R^1$, $R^2$, $R^5$, $R^6$, $R^7$, $R^8$, $R^9$, $R^{10}$ and $R^{11}$ are in general carried out by methods known from the literature, where the reduction of aldehydes or alkoxycarbonyl compounds to alcohols (a), the reduction of double bonds (b) and the alkylation (c) are to be illustrated by way of example by the following:

a) The reduction of carbonyl compounds to the corresponding alcohols is in general carried out using hydrides, such as lithiumaluminum hydride or sodium borohydride, preferably in the case of the alkoxycarbonyl compounds using lithium aluminum hydride and in the case of the aldehydes preferably using sodium borohydride in inert solvents such as ethers, hydrocarbons or alcohols or their mixtures, preferably in ethers such as, for example, diethyl ether, tetrahydrofuran or dioxane, or alcohols such as ethanol, in the case of the aldehydes preferably using sodium borohydride in ethanol, in a temperature range from 0° C. to +150° C., preferably from +20° C. to +100° C., at normal pressure.

The reduction of a double bond is in general carried out by hydrogenation with hydrogen in the presence of a catalyst such as, for example, platinum or platinum oxides, rhodium, ruthenium, chlorotris(triphenylphosphine)rhodium, or palladium on animal carbon, preferably using palladium on animal carbon in a temperature range from 0° C. to +150° C., preferably from +25° C. to +100° C.

b) Suitable solvents for the hydrogenation are protic solvents such as, for example, methanol, ethanol and/or aprotic solvents such as, for example, tetrahydrofuran, toluene, dimethylformamide, methylene chloride, dioxane or ethyl acetate.

The hydrogenation is carried out at a pressure from 1 to 300 atm, preferably at 1 to 20 atm.

c) The alkylation is in general carried out in one of the abovementioned solvents using alkylating agents such as, for example, ($C_1$-$C_8$)-alkyl halides, sulfonic acid esters or substituted or unsubstituted ($C_1$–$C_8$)-dialkyl or ($C_1$–$C_8$)-diaryl sulfates, preferably methyl iodide, p-toluenesulfonic acid esters or dimethyl sulfate.

The compounds of the general formula (II) are known in some cases or are new and can then be prepared, for example, by reacting anthracene or its substituted derivatives, such as maleic anhydride or its substituted derivatives, such as, for example, citraconic anhydride, in one of the abovementioned solvents, preferably toluene or xylene, in a temperature range of 100°–150° C., preferably at 140° C., or reacting in an aprotic solvent, such as, for example, methylene chloride, in the presence of one of the abovementioned Lewis acids, for example aluminum chloride, in a temperature range from 0° C. to 80° C., preferably at room temperature to +40° C.

The compounds of the general formulae (III), (V), (VII), (VIII) and (X) are known per se or can be prepared by customary methods.

The compounds of the general formula (IX) are known in some cases or are new and can then be prepared as described above.

The compounds of the general formula (IV) are likewise known in some cases or are new and can then be prepared, for example, as described above for the compounds of the general formula (II), by reaction of anthracene or its substituted derivatives with substituted or unsubstituted succinimides.

The compounds of the general formula (VI) are new and can be prepared, for example, as described above.

The compounds of the general formula (I) according to the invention surprisingly show an immunomodulating action.

They are thus suitable for the treatment of rheumatoid arthritis, multiple sclerosis, muscle weakness, disseminated lupus erythematosus, Basedow's disease, psoriasis, transplant rejection, Hashimoto's thyroiditis, inflammatory gastric diseases, inflammations of the gastrointestinal tract, primary cirrhosis of the liver and autoimmune hemolytic anemia.

Adjuvant Arthritis model in the Rat

Freund's adjuvant (FA) is prepared by addition of 10 mg/ml of heat-killed Mycobacterium butyricum to extra-heavy mineral oil. Lewis rats receive a 0.1 ml injection of FA (1 mg/animal) subcutaneously in the right hind paw. An acute inflammation takes place there, which is characterized by reddening, edema and a predominant neutrophilic cell infiltration (primary reaction). Tumescent areas in the treated paw on day 5 are followed between day 10–12 by an increase in the swelling (chronic inflammatory reaction) and the occurrence of a swelling in the opposite untreated paw (secondary immune response).

The cell infiltration of the chronic inflammation and the second immune response are mainly mononuclear, which indicates the presence of T-cell mediated immunity. The animals are observed daily, and the swelling is measured in millimeters on days 12 and 16 using a hand-adjustable micrometer. The swelling reaches its peak on the 16th day, on which the animals are sacrificed and tissue samples are taken for histological evaluation.

The extent of the swelling is determined by calculation of the greatest difference in the malleolus diameter between the 16th and the 0th day.

The animals receive the compounds according to the invention in a suspension of 5% polyethylene glycol and 0.5% Tween 80 in phosphate buffer solution p.o. or i.p. on days 0, 1, 2, 5, 7, 9, 12 and 14 [cf. for this purpose L. Sokoloff, 1984, Int. Rev. Exp. Pathol. 26, 107; M. E. J. Bittingham et al., 1989, J. Exp. Med. 171, 339; K. M. Conholly et al., 1989, Agents and Actions 27, 328].

TABLE A

| Ex. No. | Inhibition of the swelling (%), after administration of 10 mg/kg i.p. |
|---|---|
| 2 | 4 |
| 11 | 32 |
| 29 | 24 |
| 30 | 47 |
| 33 | 33 |
| 39 | 20 |
| 40 | 29 |
| 58 | 40 |
| 59 | 53 |
| 60 | 40 |
| 61 | 50 |
| 62 | 90 |
| 63 | 26 |
| 64 | 76 |
| 71 | 82 |
| 72 | 87 |
| 74 | 76 |
| 82 | 35 |
| 87 | 22 |
| 88 | 73 |
| 89 | 42 |
| 90 | 45 |
| 91 | 18 |
| 108 | 55 |
| 109 | 34 |

The in vitro activity of the compounds according to the invention results from their capability to inhibit T cell proliferation, which is previously stimulated by serotonin.

Inhibition of 5-HT-dependent T Cell Proliferation

Peripheral mononuclear blood cells (PBMC) are obtained from the buffy coat of the blood of healthy subjects. After isolation by means of isolymph gradients (Pharmacia), the PBMC are washed twice and used directly. Purified T cells are obtained by E rosette formation with sheep erythrocytes [cf. Blue, M.-L. , J. F. Daley, H. Levine, K. A. Craig and S. F. Schlossmann, 1986, Biosynthesis and surface expression of T8 by peripheral blood T4+cells in vitro, J. Immunol. 137, 1202]. Monocytes are partially removed by adhesion to tissue culture plates or flasks. PBMC, T cells or purified T cells (depleted in monocytes) at $5 \times 10^5$/ml, 100 µl/well are cultured in RPMI 1640 medium with 10% fetal calf serum (GIBCO) and L-glutamine in 96-well microculture plates (Becton—Dickinson) under a 5% $CO_2$ atmosphere at 37° C. for 7 days. The cultures are treated with 1 µCi of $^3$H-thymidine for 6 h on the 7th day and collected on filter paper, and the incorporated radioactivity is determined by means of liquid scintillation counting.

The test substances are dissolved in 10 mM HCl in order to achieve a final concentration of 1 mM in each case. The compounds are diluted serially 3×with medium in order to obtain a final concentration between 33 µM–0.1 µM. PWM (1:200, pokeweed mitogen) and 5-HT (100 µm, serotonin), which contain the test substances, are added to monocyte-free human T cells. The positive control (maximum proliferation) is obtained from cultures containing T cells, PWM and 5-HT. The negative control (minimal proliferation) is obtained from cultures containing T cells and PWM without 5-HT. The inhibitory activity of the test substances is expressed as the $IC_{50}$ in $\mu M$. (see also WO 92/04015)

TABLE B

| Ex. No. | $IC_{50}$ |
| --- | --- |
| 1 | >10 |
| 3 | >10 |
| 4 | 5 |
| 5 | >10 |
| 6 | >10 |
| 7 | >10 |
| 8 | >10 |
| 9 | >10 |
| 10 | >10 |
| 11 | >10 |
| 12 | >10 |
| 13 | >10 |
| 14 | >10 |
| 15 | >10 |
| 16 | >10 |
| 17 | >10 |
| 18 | >10 |
| 19 | >10 |
| 20 | >10 |
| 21 | >10 |
| 22 | >10 |
| 23 | >10 |
| 24 | >10 |
| 25 | >10 |
| 26 | >10 |
| 28 | >10 |
| 29 | >10 |
| 30 | 5 |
| 31 | >10 |
| 32 | >10 |
| 33 | >10 |
| 34 | >10 |
| 35 | >10 |
| 36 | >10 |
| 37 | >10 |
| 38 | >10 |
| 39 | >10 |
| 40 | 5 |
| 44 | >10 |
| 45 | >10 |
| 46 | >10 |
| 48 | 10 |
| 49 | >50 |
| 51 | 50 |
| 58 | 5 |
| 59 | 3 |
| 60 | 5 |
| 61 | 5 |
| 62 | 5 |
| 63 | 0.5 |
| 64 | 1 |
| 65 | 0.5 |
| 66 | 2 |
| 67 | 2 |
| 68 | 5 |
| 69 | 0.6 |
| 70 | 0.5 |
| 71 | 5 |
| 72 | 2 |
| 73 | 2 |
| 74 | 0.6 |
| 75 | 2 |
| 76 | 2 |
| 77 | 7 |
| 78 | 5 |
| 79 | 1 |
| 80 | 5 |
| 82 | 5 |
| 83 | 7 |
| 84 | 2 |
| 85 | 3 |
| 86 | 3 |
| 87 | 5 |
| 88 | 1 |
| 89 | 1 |
| 90 | 5 |
| 91 | 5 |
| 92 | 2 |

TABLE B-continued

| Ex. No. | $IC_{50}$ |
| --- | --- |
| 93 | 10 |
| 94 | 7 |
| 95 | 5 |
| 96 | >10 |
| 97 | 10 |
| 98 | 10 |
| 99 | 8 |
| 100 | 2 |
| 101 | 1 |
| 102 | 2 |
| 103 | 2 |
| 104 | 2 |
| 105 | 2 |
| 106 | 0.5 |
| 107 | 1 |
| 108 | 4 |
| 109 | 5 |
| 110 | 2 |
| 111 | 10 |
| 112 | 5 |
| 113 | 2 |
| 114 | 2 |
| 115 | 2 |
| 116 | 2 |
| 117 | 2 |

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, optionally using emulsifiers and/or dispersants, it being possible, for example, where water is used as the diluent, optionally to use organic solvents as auxiliary solvents.

Administration is carried out in a customary manner, preferably orally or parenterally, in particular perlingually or intravenously.

In the case of parenteral administration, solutions of the active compound can be employed using suitable liquid excipient materials.

In general, it has proven advantageous in the case of intravenous administration to administer amounts from 0.001 to 1 mg/kg, preferably about 0.01 to 0.5 mg/kg of bodyweight to achieve effective results, and in the case of oral administration the dose is about 0.01 to 20 m/kg, preferably 0.1 to 10 mg/k of body weight.

In spite of this, it may sometimes be necessary to deviate from the amounts mentioned, in particular depending on the body weight or on the type of application route, on individual behavior toward the medicament, the manner of its formulation and the time or interval at which administration takes place. Thus, in some cases it may be sufficient to manage with less than the abovementioned minimum amount, while in other cases the upper limit mentioned must be exceeded. In the case of the administration of relatively large amounts, it may be advisable to divide these into several individual doses over the course of the day.

STARTING COMPOUNDS

Example I 9,10-Dihydro-9,10[3', 4']-furanoanthracene-12,14(11H,15H)-dione

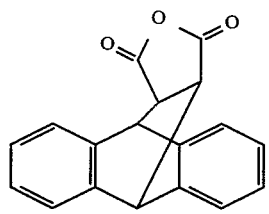

180 g (1.01 mol) of anthracene are suspended in 1000 ml of xylene together with 100 g (1.02 mol) of maleic anhydride. The suspension goes into solution on heating to 140° C. and precipitates again after boiling under reflux for 10 min. After cooling to room temperature, the precipitated cream-colored crystals are washed with xylene and ether and dried.

Melting point: 261°–263° C.
Yield: 259.9 g (92.8%)

Example II

4-[4-(4-Fluorophenyl)-piperazin-1-yl]-propionitrile

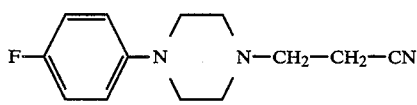

100 g (0.55 mol) of 1-(4-fluorophenyl)-piperazine are dissolved in 300 ml of toluene and treated with 0.9 ml of diazabicycloundecene (DBU). 63.2 ml (0.96 mol) of acrylonitrile are added dropwise with stirring and ice-cooling in the course of 20 min such that the temperature is kept below 30° C. After 24 h, the mixture is cooled to 10° C.; the precipitated colorless crystals are washed with ether/petroleum ether 1:1 and dried (97.4 g). A further 30.5 g are obtained after concentration of the mother liquor.

Melting point 84°–86° C.
Yield: 127.9 g (98.8%)

Example III

3-[4-(4-Fluorophenyl)-piperazin-1-yl]propylamine

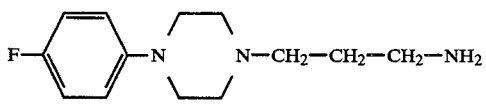

127.5 g (0.547 mol) of the compound from Example II are hydrogenated in a steel autoclave in 250 ml of methanol and 100 ml of liquid ammonia using 30 g of Raney nickel/iron=85:15 at 100–120 bar and 90° C. for about 5 h. After filtering off the catalyst with suction, it is washed with methanol and the mother liquor is concentrated in a rotary evaporator. The oily residue is titrated with ether/petroleum ether and the colorless crystals are filtered off with suction.

Melting point: 56°–58° C.
Yield: 96.1 g (74%)

Example IV 9,10-Dihydro-9,10[3', 4']-11-methyl-furanoanthracene-12,14-(11H,15H)-dione

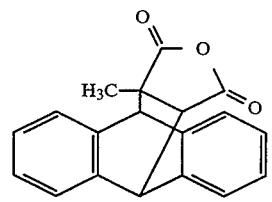

1 g (0.0056 tool) of anthracene and 0.63 g (0.0056 tool) of citraconic anhydride in 30 ml of methylene chloride p.A. are stirred in a heated flask under argon and treated in portions with 0.75 g (0.0056 tool) of aluminum chloride. After stirring at room temperature for 4 h, the black solution is poured into ice-water. After extracting twice with methylene chloride, the organic phase is washed twice with water, dried using sodium sulfate and concentrated in a rotary evaporator in a water jet vacuum. The oil which remains is triturated with ether/petroleum ether=1:1 and the crystalline precipitate is filtered off with suction.

Melting point: 158°–161° C.
Yield: 1.3 g (80%)

Preparation Examples

Example 1

13-{3-[4-(4-Fluorophenyl)piperazin-1-yl]-propyl}-9,10-dihydro-9,10[3', 4']-pyrroloanthracene-12,14(11H,15H) dione

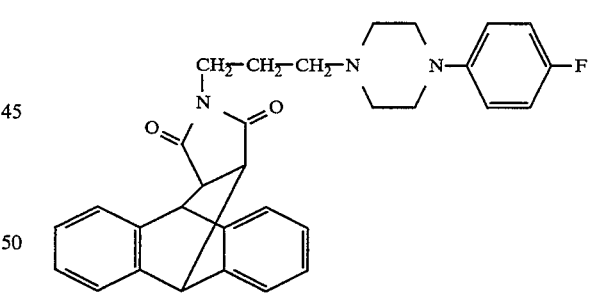

7.9 g (0.028 mol ) of the compound from Example I are suspended in 100 ml of xylene together with 7.8 g (0.03 mol) of the compound from Example III and the mixture is boiled under reflux in a water separator for 1.5 h. After cooling to room temperature, the solution is allowed to stand for 3 h and the precipitated colorless crystals are filtered off with suction, washed with ether/petroleum ether and dried (9.5 g). A further 4.4 g of the title compound is obtained after concentration of the mother liquor.

Melting point: 162°–164° C.
Yield: 13.9 g (98%)

The examples shown in Tables 1, 2 and 3 are prepared in an analogy to the procedure of Example 1:

TABLE 1

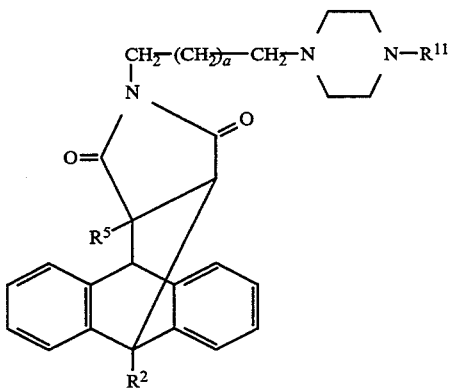

| Ex. No. | $R^2$ | $R^5$ | a | $R^{11}$ | m.p. °C. |
|---|---|---|---|---|---|
| 2 | H | H | 1 | p-Cl—$C_6H_4$ | 149–151 |
| 3 | H | H | 0 | —$C_6H_5$ | 266 |
| 4 | H | H | 2 | —$C_6H_5$ | 190 |
| 5 | H | H | 2 | p-F—$C_6H_4$ | 144 |
| 6 | H | H | 2 | o-F—$C_6H_4$ | 140 |
| 7 | H | H | 1 | —$C_6H_5$ | 193–195 |
| 8 | H | H | 2 | o-$CH_3$—$C_6H_4$ | 150 |
| 9 | H | H | 1 | p-F—$C_6H_4$ | 158–160 |
| 10 | H | H | 1 | p-$CF_3$—$C_6H_4$ | 180–182 |
| 11 | H | H | 1 | p-$CH_3$—$C_6H_4$ | 174–176 |
| 12 | H | H | 1 | p-$OCH_3$—$C_6H_4$ | 174–176 |
| 13 | H | H | 1 | m-Cl—$C_6H_4$ | 98–100 |
| 14 | H | H | 1 | m-$CH_3$—$C_6H_4$ | 165–168 |
| 15 | H | H | 1 | m-$CF_3$—$C_6H_4$ | 125–127 |
| 16 | H | H | 1 | m-$OCH_3$—$C_6H_4$ | 135–137 |
| 17 | H | H | 1 | o-Cl—$C_6H_4$ | 180–182 |
| 18 | H | H | 1 | o-F—$C_6H_4$ | 204–206 |
| 19 | H | H | 1 | o-$CH_3$—$C_6H_4$ | 223–225 |
| 20 | H | H | 1 | o-$C_2H_5$—$C_6H_4$ | 177–179 |
| 21 | H | H | 1 | o-$OCH_3$—$C_6H_4$ | 197–200 |
| 22 | H | H | 1 | o-$OC_2H_5$—$C_6H_4$ | 139–141 |
| 23 | H | H | 1 | o,o-$CH_3$—$C_6H_3$ | 148–150 |
| 24 | H | H | 1 | o,m-$CH_3$—$C_6H_3$ | 188–190 |
| 25 | H | H | 1 | o,p-$CH_3$—$C_6H_3$ | 155–157 |
| 26 | H | H | 1 | o,m-$CH_3$—$C_6H_3$ | 218–220 |
| 27 | H | H | 1 | m,p-$CH_3$—$C_6H_4$ | 108–110 |
| 28 | H | H | 1 | m,p-$OCH_3$—$C_6H_3$ | 106–108 |
| 29 | —$CH_3$ | H | 1 | —$C_6H_5$ | 172–174 |
| 30 | —$CH_3$ | H | 1 | p-Cl—$C_6H_4$ | 144–147 |
| 31 | —$CH_3$ | H | 1 | p-F—$C_6H_4$ | 127–129 |
| 32 | —$CH_2OH$ | H | 1 | —$C_6H_5$ | 214–216 |
| 33 | —$CH_2OH$ | H | 1 | p-F—$C_6H_4$ | 188–190 |
| 34 | —Cl | H | 1 | —$C_6H_5$ | 187–188 |
| 35 | —Cl | H | 1 | p-F—$C_6H_4$ | 165–167 |
| 36 | —CN | H | 1 | p-F—$C_6H_4$ | 199–201 |
| 37 | —CH=$CH_2$ | H | 1 | p-F—$C_6H_4$ | 135–137 |
| 38 | —CH=CH—$C_6H_5$ | H | 1 | p-F—$C_6H_4$ | 170–173 |
| 39 | H | —$CH_3$ | 1 | —$C_6H_5$ | 164–166 |
| 40 | H | —$CH_3$ | 1 | p-F—$C_6H_5$ | 126–128 |
| 41 | H | H | 1 | m,m-Cl—$C_6H_3$ | 165–168 |
| 42 | H | H | 1 | m,m,p-$OCH_3$—$C_6H_2$ | 157–159 |
| 43 | —$CH(OCH_3)_2$ | H | 1 | p-F—$C_6H_4$ | 218–200 |

TABLE 2

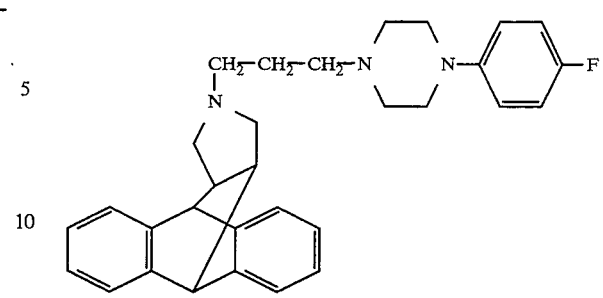

| Ex. No. | R¹ | R² | R¹¹ | m.p. °C. |
|---|---|---|---|---|
| 44 | —CH₃ | —CH₃ | p-F—C₆H₄ | 132–134 |
| 45 | —Br | —Br | p-F—C₆H₄ | 178–181 |
| 46 | —Cl | —Cl | p-C₆H₅ | 139–141 |

TABLE 3

| Ex. No. | R¹ | R² | R⁵ | R⁶ | R¹¹ | m.p. °C. |
|---|---|---|---|---|---|---|
| 47 | Cl | Cl | H | H | P-F—C₆H₄ | 134–136 |
| 48 | H | —CH₂Cl | H | H | p-F—C₆H₄ | 150–153 |
| 49 | —C₆H₅ | H | H | H | p-F—C₆H₄ | 188–190 |
| 50 | H | H | —C₆H₅ | H | p-F—C₆H₄ | 193–196 |
| 51 | H | H | Cl | —Cl | p-F—C₆H₄ | 168–171 |
| 52 | Br | —Br | H | H | —C₆H₅ | 215–218 |
| 53 | H | —CH₂—NH—CH₃ | H | H | p-F—C₆H₄ | 163–165 |
| 54 | H | —OH | H | H | p-F—C₆H₄ | 105–107 (dec.) |
| 55 | H | —Cl | —CH₃ | H | p-F—C₆H₄ | 94–98 |
| 56 | H | H | —CH₃ | —CH₃ | p-F—C₆H₄ | 165.8–167.8 |
| 57 | H | H | —F | —F | p-F—C₆H₄ | 142–144 |

Example 58

13-{3-[4-(4-Fluorophenyl)-piperazin-1-yl]propyl}-9,10,11,12,14,15-hexahydro-9,10[3′, 4′]pyrroloanthracene 100 ml of absolute dioxane are initially introduced into a heated flask under argon and 2.5 g (0.065 mol) of lithium aluminum hydride are suspended with stirring. After heating to 90° C., 11 g (0.022 mol) of the compound from Example 1 are added in portions in the course of 10 min. The suspension is then boiled under reflux for 6 h. After cooling to room temperature, 2.5 ml of water and 7.5 ml of dil. KOH are added dropwise successively with vigorous stirring, the mixture is boiled under reflux for 10 min, and the voluminous precipitate is filtered off hot with suction and washed with dioxane.

After concentration of the mother liquor in a rotary evaporator, the oily residue is dissolved in methylene chloride, the solution is washed twice with water and the organic phase is dried using sodium sulfate and concentrated in a rotary evaporator. The oil which remains is triturated with ether/petroleum ether and the colorless crystals are filtered off with suction and dried.

Melting point: 94°–96° C.

Yield: 85.7%

The compounds shown in Tables 4, 5 and 6 are prepared in analogy to the procedure of Example 58:

TABLE 4

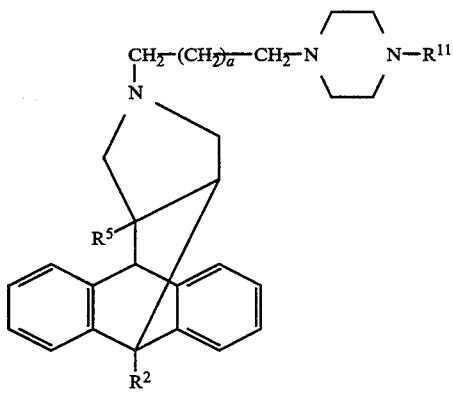

| Ex. No. | R[2] | R[5] | a | R[11] | m.p. °C. | Salt* |
|---|---|---|---|---|---|---|
| 59 | H | H | 1 | p-Cl—C₆H₄ | 126–128 | |
| 60 | H | H | 0 | —C₆H₅ | 157 | |
| 61 | H | H | 1 | —C₆H₅ | 192 | 2 × A |
| 62 | H | H | 2 | —C₆H₅ | 143 | |
| 63 | H | H | 3 | —C₆H₅ | 165 | 2 × B |
| 64 | H | H | 4 | —C₆H₅ | 108 | |
| 65 | H | H | 2 | o-Cl—C₆H₄ | 114 | |
| 66 | H | H | 2 | m-Cl—C₆H₄ | 146 | |
| 67 | H | H | 2 | p-Cl—C₆H₄ | 133 | |
| 68 | H | H | 2 | m,p-Cl—C₆H₃ | 127 | |
| 69 | H | H | 2 | p-F—C₆H₄ | 126 | |
| 70 | H | H | 2 | p-OCH₃—C₆H₄ | 135 | |
| 71 | H | H | 2 | o-OCH₃—C₆H₄ | 98 | |
| 72 | H | H | 2 | o-F—C₆H₄ | 147 | |
| 73 | H | H | 2 | p-CF₃—C₆H₄ | 143 | |
| 74 | H | H | 2 | p-CH₃—C₆H₄ | 126 | |
| 75 | H | H | 1 | p-CF₃—C₆H₄ | 131–133 | |
| 76 | H | H | 1 | p-CH₃—C₆H₄ | 98–100 | |
| 77 | H | H | 1 | p-OCH₃—C₆H₄ | 87–89 | |
| 78 | H | H | 1 | m-Cl—C₆H₄ | 188–190 (dec.) | 1.5 × B |
| 79 | H | H | 1 | m-CH₃—C₆H₄ | 87–89 | |
| 80 | H | H | 1 | m-CF₃—C₆H₄ | 188–190 (dec.) | 1.5 × B |
| 81 | H | H | 1 | m-OCH₃—C₆H₄ | 110–112 | |
| 82 | H | H | 1 | o-Cl—C₆H₄ | 194–196 (dec.) | 2 × B |
| 83 | H | H | 1 | o-F—C₆H₄ | 83–85 | |
| 84 | H | H | 1 | o-CH₃—C₆H₄ | 201–203 (dec.) | 2 × B |
| 85 | H | H | 1 | o-C₂H₅—C₆H₄ | 193–195 | 2 × B |
| 86 | H | H | 1 | o-OCH₃—C₆H₄ | 80–82 | |
| 87 | H | H | 1 | o-OC₂H₅—C₆H₄ | 200–202 (dec.) | 1.5 × B |
| 88 | H | H | 1 | o,o-CH₃—C₆H₃ | 123–125 | |
| 89 | H | H | 1 | o,m-CH₃—C₆H₃ | 205–207 (dec.) | 2 × B |
| 90 | H | H | 1 | o,p-CH₃—C₆H₃ | 204–206 (dec.) | 2 × B |
| 91 | H | H | 1 | o,m-CH₃—C₆H₃ | 206–208 (dec.) | 2 × B |
| 92 | H | H | 1 | m,p-CH₃—C₆H₃ | 100–102 | |
| 93 | H | H | 1 | m,p-OCH₃—C₆H₃ | 168–171 (dec.) | 2 × B |
| 94 | —CH₃ | H | 1 | —C₆H₅ | 125–127 | |
| 95 | —CH₃ | H | 1 | p-Cl—C₆H₄ | 131–133 | |
| 96 | —CH₃ | H | 1 | p-F—C₆H₄ | 113–115 | |
| 97 | —CH₂OH | H | 1 | —C₆H₅ | 173–175 | |
| 98 | —CH₂OH | H | 1 | p-F—C₆H₄ | 150–152 | |
| 99 | —Cl | H | 1 | —C₆H₅ | 118–120 | |
| 100 | —Cl | H | 1 | p-F—C₆H₄ | 128–130 | |
| 101 | —CH₂NH₂ | H | 1 | p-F—C₆H₄ | 120–122 | |
| 102 | —CH=CH₂ | H | 1 | p-F—C₆H₄ | 140–142 | |
| 103 | —CH=CH—C₆H₅ | H | 1 | p-F—C₆H₄ | 70–74 | |
| 104 | H | —CH₃ | 1 | —C₆H₅ | 108–110 | |
| 105 | H | —CH₃ | 1 | p-F—C₆H₄ | 88–90 | |
| 106 | H | H | 1 | -m,m,p-OCH₃—C₆H₂ | 144–146 | |
| 107 | —CH(OCH₃)₂ | H | 1 | p-F—C₆H₄ | 132–134 | |
| 108 | H | H | 1 | p—Cl—C₆H₄ | 148–150 | 1 × B |

TABLE 4-continued
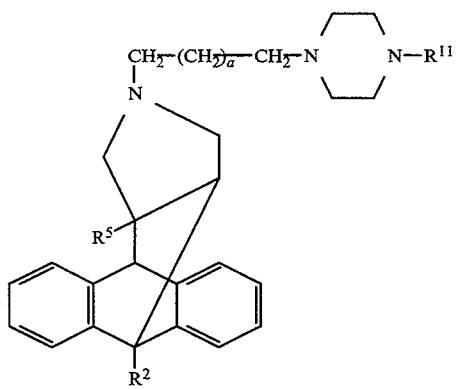
| Ex. No. | R² | R⁵ | a | R¹¹ | m.p. °C. | Salt* |
|---|---|---|---|---|---|---|
| 109 | H | H | 1 | p-Cl—C₆H₄ | 313–315 (dec.) | 1 × C |
A = HCl
B = —H₂OC—CH=CH—CO₂H
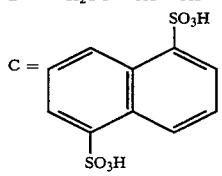
TABLE 5
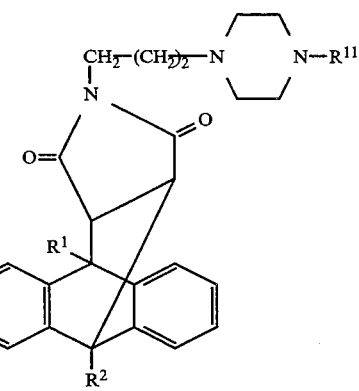
| Ex. No. | R¹ | R² | R¹¹ | m.p. °C. |
|---|---|---|---|---|
| 110 | —CH₃ | CH₃ | p-F—C₆H₄ | 161–163 |
TABLE 5-continued
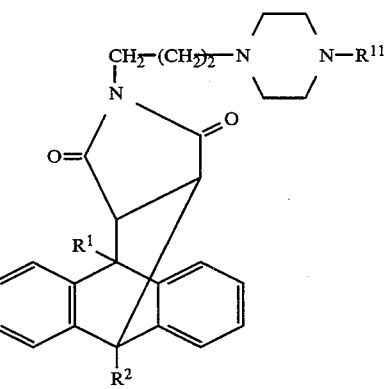
| Ex. No. | R¹ | R² | R¹¹ | m.p. °C. |
|---|---|---|---|---|
| 111 | —Br | —Br | p-F—C₆H₄ | 172–175 |

TABLE 6

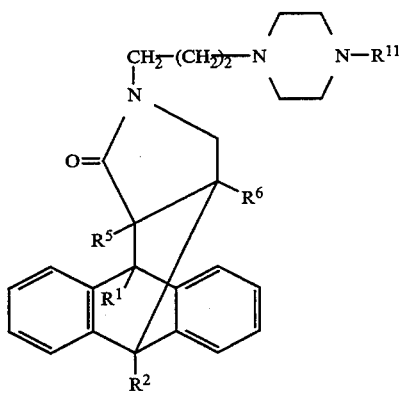

| Ex. No. | R¹ | R² | $R_5$ | $R^6$ | $R^{11}$ | m.p. °C. | Salt* |
|---|---|---|---|---|---|---|---|
| 112 | Cl | Cl | H | H | p-F—$C_6H_4$ | 168–170 | |
| 113 | H | —$CH_2Cl$ | H | H | p-F—$C_6H_4$ | 88–90 | |
| 114 | —$C_6H_5$ | H | H | H | p-F—$C_6H_4$ | 164–166 | |
| 115 | H | H | H | H | m,m-Cl—$C_6H_3$ | 132–134 | |
| 116 | Cl | Cl | H | H | —$C_6H_5$ | 166–168 | |
| 117 | H | H | —$C_6H_5$ | H | p-F—$C_6H_4$ | 126–128 | |
| 118 | H | OH | H | H | p-F—$C_6H_4$ | 123–125 (dec.) | 2 × B |
| 119 | H | —Cl | $CH_3$ | H | p-F—$C_6H_4$ | 124–126 | |
| 120 | H | —$CH_2$—NH—$CH_3$ | H | H | p-F—$C_6H_4$ | Oil | |
| 121 | Br | Br | H | H | —$C_6H_5$ | 175.8–176.8 | |
| 122 | H | H | F | F | p-F—$C_6H_4$ | 59–61 | |
| 123 | H | H | $CH_3$ | $CH_3$ | p-F—$C_6H_4$ | 128.8–129.4 | |

*B = $H_2OC$—CH═CH.$CO_2H$

We claim:
1. A piperazine-substituted pyrroloanthracene of the formula (I)

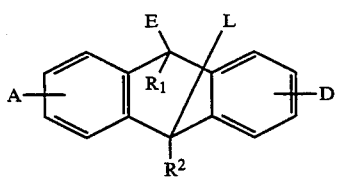

in which
A and D are identical or different and represent hydrogen, hydroxyl, halogen, cyano, carboxyl, nitro, trifluoromethyl or trifluoromethyloxy, or represent straight-chain or branched alkyl or alkoxy in each case having up to 8 carbon atoms, $R^1$ and $R^2$ are identical or different and represent hydrogen, halogen, cyano, formyl, phenyl or hydroxyl, or represent straight-chain or branched alkoxy having up to 8 carbon atoms, or represent straight-chain or branched alkyl or alkenyl in each case having up to 8 carbon atoms, each of which is optionally substituted up to 2 times by identical or different hydroxyl, nitro, phenyl or halogen, by straight-chain or branched alkoxy having up to 6 carbon atoms or by a group of the formula —$NR^3R^4$, in which
$R^3$ and $R^4$ are identical or different and denote hydrogen, straight-chain or branched alkyl having up to 6 carbon atoms or phenyl, E and L together form a heterocyclic radical of the formula

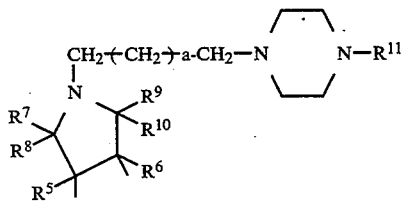

in which
$R^5$ and $R^6$ are identical or different and denote hydrogen, halogen, phenyl or straight-chain or branched alkyl having up to 8 carbon atoms, which is optionally substituted by carboxyl or by straight-chain or branched alkoxycarbonyl having up to 6 carbon atoms, $R^7$, $R^8$, $R^9$ and $R^{10}$ are identical or different and denote hydrogen or straight-chain or branched alkyl having up to 6 carbon atoms, or $R^7$ and $R^8$ and/or $R^9$ and $R^{10}$ in each case together form the radical of the formula═O, a denotes a number 0, 1, 2, 3, 4, 5 or 6, $R^{11}$ denotes aryl having 6 to 10 carbon atoms, which is optionally substituted up to 3 times by identical or different halogen, hydroxyl, nitro, cyano, trifluoromethyl, trifluoromethoxy or by straight-chain or branched alkyl or alkoxy in each case having up to 8 carbon atoms, or a pharmaceutically acceptable salt thereof.

2. A piperazine-substituted pyrroloanthracene or salt thereof as claimed in claim 1
in which
A and D are identical or different and represent hydrogen, hydroxyl, fluorine, chlorine, bromine, carboxyl, nitro, trifluoromethyl, trifluoromethoxy or represent straight-chain or branched alkyl or alkoxy in each case having up to 6 carbon atoms, $R^1$ and $R^2$ are identical or different and represent hydrogen, fluorine, chlorine, bromine, cyano, formyl, phenyl or hydroxyl, or represent straight-chain or branched alkoxy having up to 6 carbon atoms, or represent straight-chain or branched alkyl or alkenyl in each case having up to 6 carbon atoms, each of which is optionally substituted up to 2 times by identical or different hydroxyl, nitro, phenyl, fluorine, chlorine or bromine, by straight-chain or branched alkoxy having up to 4 carbon atoms or by a group of the formula $-NR^3R^4$, in which $R^3$ and $R^4$ are identical or different and denote hydrogen, straight-chain or branched alkyl having up to 4 carbon atoms or phenyl, E and L together form a heterocyclic radical of the formula

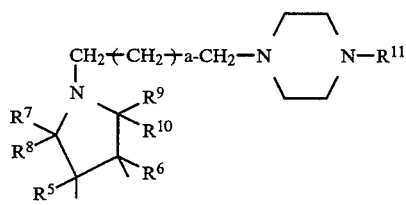

in which $R^5$ and $R^6$ are identical or different and denote hydrogen, fluorine, chlorine, bromine, phenyl or straight-chain or branched alkyl having up to 6 carbon atoms, which is optionally substituted by carboxyl or by straight-chain or branched alkoxycarbonyl having up to 4 carbon atoms, $R^7$, $R^8$, $R^9$ and $R^{10}$ are identical or different and denote hydrogen or straight-chain or branched alkyl having up to 4 carbon atoms, or $R^7$ and $R^8$ and/or $R^9$ and $R^{10}$ in each case together form the radical of the formula $=O$, a denotes a number 0, 1, 2, 3, 4 or 5, $R^{11}$ denotes phenyl which is optionally substituted up to 3 times by identical or different fluorine, chlorine, bromine, hydroxyl, nitro, cyano, trifluoromethyl or trifluoromethoxy or by straight-chain or branched alkyl or alkoxy in each case having up to 6 carbon atoms.

3. A piperazine-substituted pyrroloanthracene or salt thereof as claimed in claim 1 in which

A and D are identical or different and represent hydrogen, hydroxyl, fluorine, chlorine, bromine or straight-chain or branched alkyl having up to 4 carbon atoms, $R^1$ and $R^2$ are identical or different and represent hydrogen, fluorine, chlorine, bromine, cyano, formyl, phenyl or hydroxyl, or represent straight-chain or branched alkoxy having up to 4 carbon atoms, or represent straight-chain or branched alkyl or alkenyl in each case having up to 4 carbon atoms, each of which is optionally substituted up to 2 times by identical or different hydroxyl, nitro, phenyl, fluorine, chlorine or bromine, by straight-chain or branched alkoxy having up to 3 carbon atoms or by amino or aminomethyl, E and L together form a heterocyclic radical of the formula

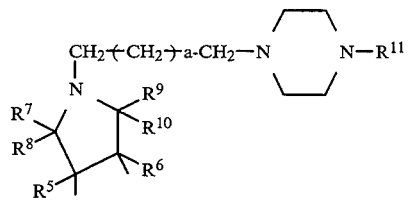

in which $R^5$ and $R^6$ are identical or different and denote hydrogen, fluorine, chlorine, bromine, phenyl or straight-chain or branched alkyl having up to 4 carbon atoms, which is optionally substituted by carboxyl or by straight-chain or branched alkoxycarbonyl having up to 3 carbon atoms, $R^7$, $R^8$, $R^9$ and $R^{10}$ are identical or different and denote hydrogen or straight-chain or branched alkyl having up to 3 carbon atoms, or $R^7$ and $R^8$ and/or $R^9$ and $R^{10}$ in each case together form the radical of the formula $=O$, a denotes a number 0, 1, 2, 3 or 4, $R^{11}$ denotes phenyl which is optionally substituted up to 3 times by identical or different fluorine, chlorine, bromine, hydroxyl, nitro, cyano, trifluoromethyl or trifluoromethoxy or by straight-chain or branched alkyl or alkoxy in each case having up to 4 carbon atoms.

4. A compound according to claim 1, wherein such compound is

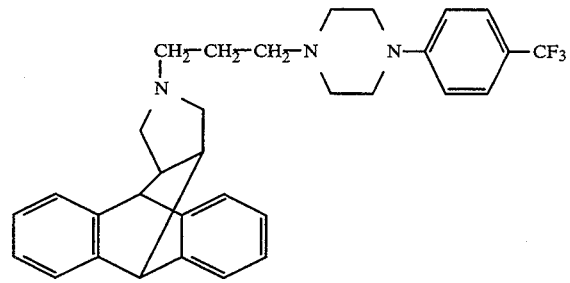

or a pharmaceutically acceptable salt thereof.

5. A compound according to claim 1, wherein such compound is

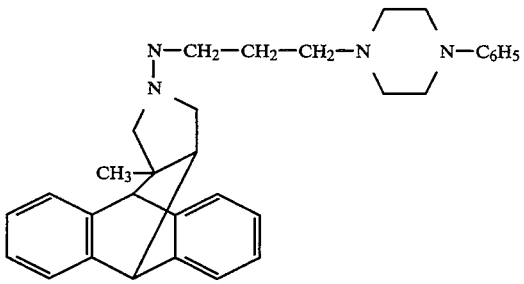

or a pharmaceutically acceptable salt thereof.

6. A composition for the treatment of rheumatoid arthritis, inflammatory gastric diseases or inflammations of the gastrointestinal tract, comprising an amount effective therefor of a compound or salt thereof according to claim 1 and a pharmaceutically acceptable carrier.

7. A method of treating rheumatoid arthritis, inflammatory gastric diseases and inflammations of the gastrointestinal tract in a patient afflicted therewith which comprises administering to such patient an amount effective therefor of a compound or salt thereof according to claim 1.

8. The method according to claim 7, wherein such compound is

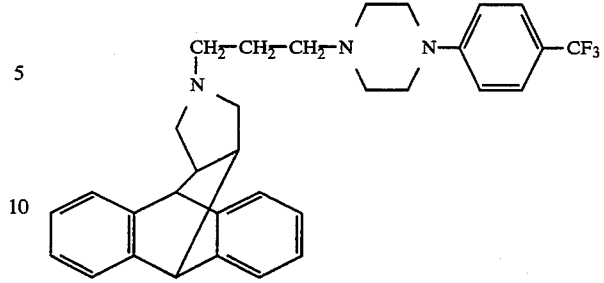

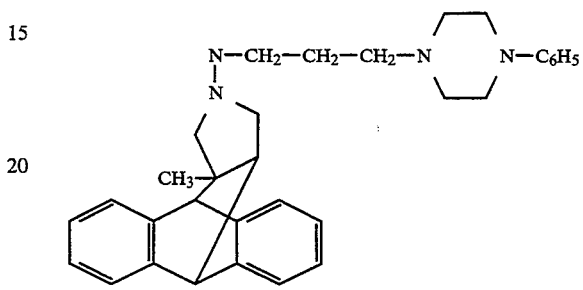

or a pharmaceutically acceptable salt thereof.

9. The method according to claim 7, wherein the patient is afflicted with rheumatoid arthritis.

10. The method according to claim 7, wherein the patient is afflicted with inflammatory gastric diseases.

11. The method according to claim 7, wherein the patient is afflicted with inflammations of the gastrointestinal tract.

* * * * *

UNITED STATES PATENT AND TRADEMARK OFFICE
CERTIFICATE OF CORRECTION

PATENT NO. : 5,409,932
DATED : April 25, 1995
INVENTOR(S) : Schwenner, et al.

It is certified that error appears in the above-indentified patent and that said Letters Patent is hereby corrected as shown below:

Col. 28, line 55   Delete "

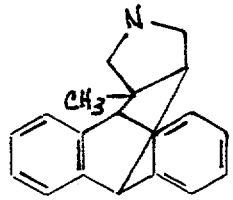                " and subsubstitute -- 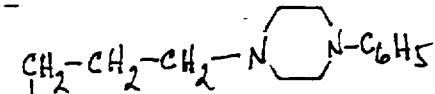

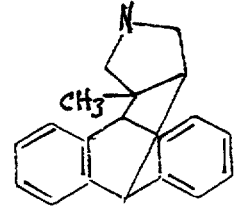                          --

Col. 30, line 15   Delete " 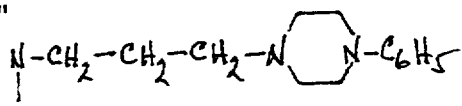

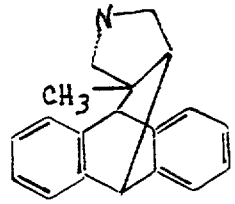                " and sub-

UNITED STATES PATENT AND TRADEMARK OFFICE
CERTIFICATE OF CORRECTION

PATENT NO. : 5,409,932
DATED : April 25, 1995
INVENTOR(S) : Schwenner, et al.

It is certified that error appears in the above-indentified patent and that said Letters Patent is hereby corrected as shown below:

Col. 30, line 15 Cont'd

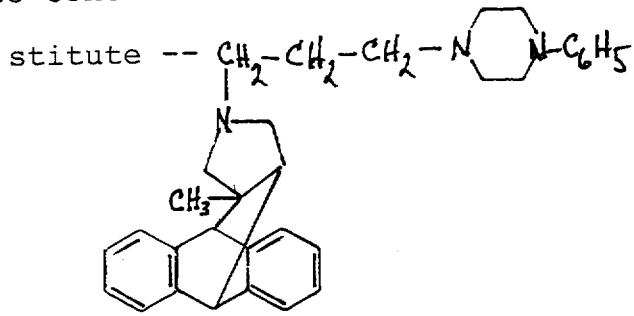

Signed and Sealed this

Twenty-fifth Day of July, 1995

Attest:

BRUCE LEHMAN

*Attesting Officer*          *Commissioner of Patents and Trademarks*